(12) United States Patent
Levin et al.

(10) Patent No.: US 7,027,627 B2
(45) Date of Patent: Apr. 11, 2006

(54) MEDICAL DECISION SUPPORT SYSTEM AND METHOD

(75) Inventors: Moshe Levin, Tel Aviv (IL); Joseph Hagler, Tel Aviv (IL); Iris Konforti, Tel Aviv (IL)

(73) Assignee: Accuramed (1999) Ltd., Tel Aviv (IL)

( * ) Notice: Subject to any disclaimer, the term of this patent is extended or adjusted under 35 U.S.C. 154(b) by 688 days.

(21) Appl. No.: 09/935,135

(22) Filed: Aug. 21, 2001

(65) Prior Publication Data

US 2002/0039434 A1    Apr. 4, 2002

(30) Foreign Application Priority Data

Aug. 28, 2000   (IL)   ..................................... 138123

(51) Int. Cl.
*G06K 9/00*   (2006.01)

(52) U.S. Cl. ........................ 382/128; 382/284; 382/294

(58) Field of Classification Search ................ 382/128, 382/274, 275, 133, 284, 294; 250/455; 356/39; 377/10; 362/575; 600/407, 300

See application file for complete search history.

(56) References Cited

U.S. PATENT DOCUMENTS

| | | | |
|---|---|---|---|
| 4,965,725 A | 10/1990 | Rutenberg | |
| 5,218,645 A | 6/1993 | Bacus | |
| 5,287,272 A | 2/1994 | Rutenberg et al. | |
| 5,297,034 A * | 3/1994 | Weinstein | ................... 382/128 |
| 5,544,650 A | 8/1996 | Boon et al. | |
| 5,740,270 A | 4/1998 | Rutenberg et al. | |
| 5,889,881 A | 3/1999 | MacAulay et al. | |
| 5,939,278 A | 8/1999 | Boon et al. | |
| 6,026,174 A | 2/2000 | Palcic et al. | |
| 6,518,968 B1 * | 2/2003 | Ritter et al. | ................ 345/426 |
| 6,674,881 B1 * | 1/2004 | Bacus et al. | ................ 382/128 |
| 6,684,092 B1 * | 1/2004 | Zavislan | ..................... 600/407 |
| 6,947,583 B1 * | 9/2005 | Ellis et al. | ................... 382/128 |
| 2002/0021828 A1 * | 2/2002 | Papier et al. | ............... 382/128 |
| 2002/0076092 A1 * | 6/2002 | Ellis et al. | ................... 382/133 |
| 2003/0036683 A1 * | 2/2003 | Kehr et al. | ................. 600/300 |
| 2003/0153819 A1 * | 8/2003 | Iliff | ............................. 600/300 |
| 2003/0163031 A1 * | 8/2003 | Madden et al. | ............. 600/300 |
| 2003/0227673 A1 * | 12/2003 | Nakagawa | ................. 359/380 |
| 2004/0071327 A1 * | 4/2004 | Ellis et al. | ................... 382/128 |
| 2004/0136581 A1 * | 7/2004 | Ellis et al. | ................... 382/128 |
| 2004/0167390 A1 * | 8/2004 | Alexander et al. | .......... 600/410 |
| 2004/0236773 A1 * | 11/2004 | Bacus et al. | ................ 707/100 |
| 2005/0123181 A1 * | 6/2005 | Freund et al. | .............. 382/128 |

* cited by examiner

*Primary Examiner*—Barry Choobin
(74) *Attorney, Agent, or Firm*—Clark & Elbing LLP

(57) ABSTRACT

A medical decision support system including a computer and a computer program product arranged to provide data derived from examination of digital images of a tissue specimen according to predetermined criteria for histopathological analysis, and a method for assisting in obtaining a pathological diagnosis from a plurality of pictures representing a specimen on a slide, the method including obtaining digitized data corresponding to images of a specimen on a slide placed under a microscope; processing the images; examining the images in accordance with predetermined histopathological criteria; and providing an examination report based on the examination.

23 Claims, 7 Drawing Sheets

MEDICAL DECISION SUPPORT SYSTEM AND METHOD

FIELD OF THE INVENTION

The present invention relates to medical decision support system and method and in particular to a system and method of examination of tissue specimens and analysis and diagnosis of benign and malignant pathologies.

BACKGROUND OF THE INVENTION

Skin cancer is the most common cancer in the US. It affects over 600,000 Americans every year, accounting for 1% of all cancer deaths. The mortality from melanoma has increased in recent years, especially in white males, possibly as a result of increased recreational exposure to sunlight.

Detection and surgical treatment of the early stages of this malignancy are usually curative. In contrast, diagnosis and treatment in late stages often have dismal results.

Histopathological examination, which is a diagnostic method of a tissue specimen, is the most important medical tool in process of diagnosis. The histopathological diagnosis of melanoma is based upon architectural (symmetry, circumscription, maturation, nests, arrangement, distribution) and cytological (atypicality, mitosis, necrosis) criteria. Every suspected melanoma to be diagnosed should be surgically excised. A biopsy is mandatory in order to establish a histopathological diagnosis. Nowadays, pathologists have known criteria list that has to be checked by the pathologist in order to diagnose the specimen. The pathological criteria are crucial in order to establish accurate diagnosis.

The following prior art publications are known to the applicant:

U.S. Pat. No. 5,297,034 discloses a system for providing pathology diagnostic opinions to physicians at sites remote from where the consulting pathologist is physically located.

U.S. Pat. No. 5,939,278 discloses a method and apparatus for semi-automating a cell classification process using at least primary and secondary classifications followed by review by a skilled technician.

U.S. Pat. No. 4,965,725 refers to a neural network based automated cytological specimen classification system and method. It discloses an automated screening system and method for cytological specimen classification.

U.S. Pat. Nos. 5,287,272, 5,544,650 and 5,740,270 relate to the same patent family of the above patents and disclose an automated cytological specimen classification systems and method based on an automated cytological specimen classifier for detection of atypical cells.

U.S. Pat. Nos. 5,889,881 and 6,026,174 teach methods and apparatus or system for automatically detecting malignancy-associated changes in cell samples. U.S. Pat. No. 5,218,645 also concerns a method and apparatus for analyzing cell objects of a cell sample for diagnosis. These methods detect malignancy in a cell sample and do not include histopathology diagnosis of the tissue. A cytological examination is a method to obtain single cells or a cluster of cells. Cytological examination does not include examination of architectural or structural cell formations, but just a smear of a single cell and for this reason is not diagnostic per se. Cytological procedure is contraindicated in the context of suspected melanoma of the skin because it is not a diagnostic procedure and furthermore, it may cause spreading of malignant cells.

The technological breakthroughs of the last few years in computers and especially the Internet have greatly affected our lives. Computers and Internet applications have entered into the realms of medicine and are a critical factor in the scientific advancement of medical research and its clinical applications.

When a patient's case is complex, rare or the person making the diagnosis is simply inexperienced, an expert system can help come up with likely diagnoses based on digital images and clinical data. Furthermore, many medical images can now be automatically interpreted, from plain X-rays through to more complex images like angiograms, CT and MRI scans. This is of value in mass-screenings, for example, when a system can flag potentially abnormal images for detailed human attention. Nevertheless, although this rapid advancement there is no current method or system that can generate a computerized histopathological examination let alone analysis or diagnosis.

In view of the above, there is a need for a computerized medical decision support system for the examination and diagnosis of benign and malignant pathologies.

SUMMARY OF THE INVENTION

The present invention aims at providing a computerized medical decision support system for examining digital images of tissue specimen. The system comprising a computer and a computer program product arranged to provide environment and data for histopathological analysis.

Further the present invention aims at providing a medical decision support system for examining digital images of tissue specimen and providing an analysis. Yet, the present invention aims at providing a medical decision support system for examining digital images of tissue specimen, analyzing the specimen and providing a diagnosis thereof.

Further the invention provides a system and method for telepathological consultation.

The present invention aims at further providing a novel decision support system capable of identifying pathological findings by using Euclidian distance among feature vectors, as known, and differentiating between various closely resembling pathologies, especially the differential diagnosis of pigmented skin lesions.

A further object of the present invention is to provide a system capable of computerized digital images processing and analysis based upon histopathological criteria resulted in computerized pathological diagnosis.

Yet a further object of the present invention is to provide a single central site able to improve its diagnostic performance from one test to another due to a unique neural network capacity.

Another object of the present invention is to provide co plot maps showing the similarity between the diagnosed case to previous cases, some of which may be malignant or/and benign.

The system of the present invention may further include a digital camera for capturing at least one picture representing pathological characteristics of a specimen on a slide (preferably more that one picture), a microscope, a computer and a computer program capable of simulating a histopathology diagnosis and provide an operator with a fully automated diagnosis.

According to a preferred embodiment, the invention also includes communication means for transferring data from the digital camera to a remote server and from the server back to the client's computer.

Furthermore, the present invention provides a method for obtaining a pathological diagnosis from at least one picture representing a pathological slide. The method includes the steps of obtaining computer files including digitized data corresponding to at least one picture of a pathological slide placed under a microscope, analyzing the images to detect objects of interest, and providing an automated pathological diagnosis.

The present invention further provides a method in which the step of analyzing include also the steps of combining pictures taken at the same magnification, enabling zooming in and out from each magnification to another, detecting background features etc.

BRIEF DESCRIPTION OF THE DRAWINGS

The present invention will be further understood from the following detailed description taken in conjunction with the drawings in which.

DETAILED DESCRIPTION OF THE INVENTION

The present invention provides a system to help pathologists diagnose pathological processes by inspecting known clinical parameters and additional parameters from histopathological slides using artificial intelligence based technology. The present invention provides a higher standard of diagnosis, that is independent of subjective factors such as tiredness, loss of concentration and lack of expertise.

This is accomplished by means of a system including an image processing module for processing at least one digital image, preferably a plurality of digital images representing a tissue sample, and providing processed images to an examination module, which examines the processed images according to predetermined criteria and provides examination data corresponding thereto. The system also includes a database including examination or/and analysis or/and diagnosis data corresponding to previous or known cases. A preferred embodiment of the invention further includes an analysis module, for analyzing the data provided by the examination module, or by an external source in appropriate form, and providing an analysis thereof. Another preferred embodiment of the invention includes a diagnostic module, for generating a diagnosis in respect of examination data provided by the examination module or an external source, preferably in conjunction with the data from known cases stored in the database.

The following description of the invention refers to the Dermatopathology field of Melanoma, by way of example.

However, it will be appreciated by any person skilled in the art that the invention is applicable to all areas of pathology by adding or arranging the system to perform examination, analysis and/or diagnosis according to suitable known criteria for that particular pathology.

Among the various types of images the ones that present the highest level of complexity are these coming from tissue lesions. This is due to the large number of different structures in each section, variation of staining between slides and on the same slide itself, and the importance of the presence of structural and cell features obtained from the slides at different magnifications. The advantage of using an automated examination and detection system is that there are some features that cannot be measured, even by an expert, in an accurate way (for example, cell size).

Figure 1:
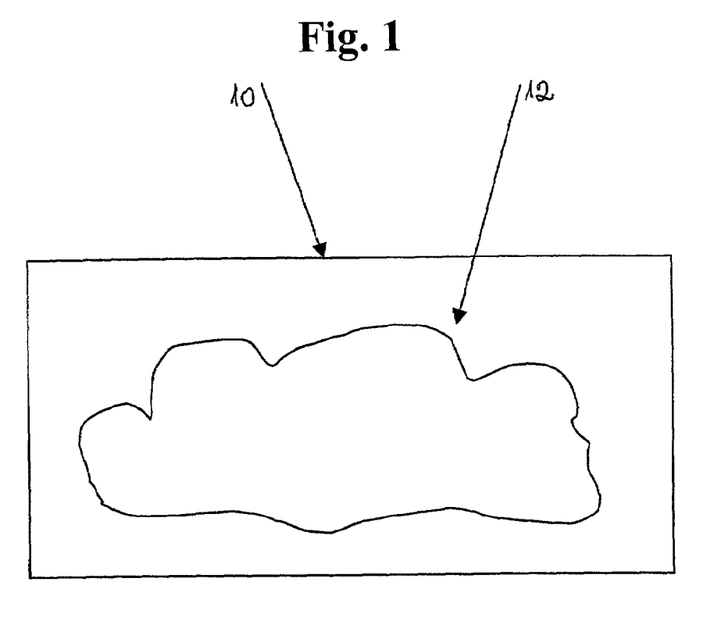
FIG. 1 is a block diagram of a typical histopathological slide from human skin tissue, according to one embodiment of the invention.
Figure 2:
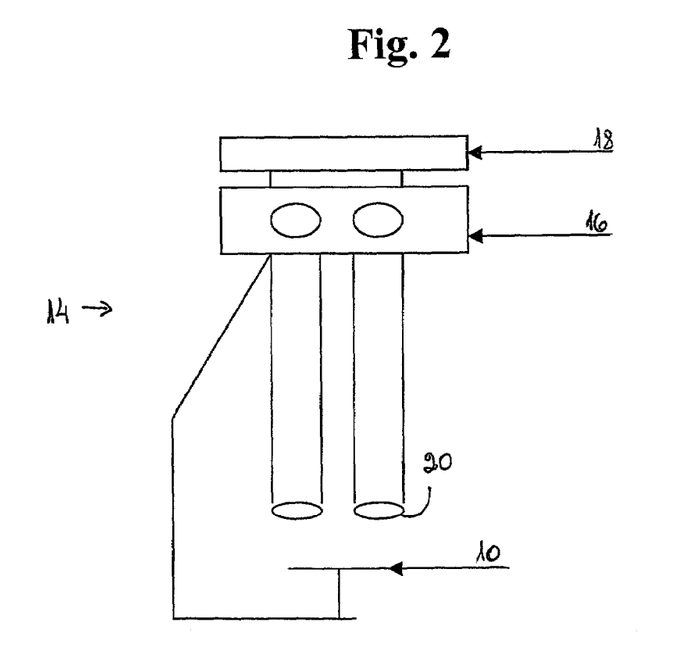
FIG. 2 is a block diagram describing the image requisition.

The present invention will hereafter be described with reference to the accompanying drawings. FIGS. 1 and 2 refer to one embodiment of the invention which includes an image acquisition module, which is optional.

Referring to FIG. 1, a block diagram of a typical input taken from a pathological slide 10 of human skin tissue 12, is shown. The slide is prepared by excising the suspected lesion from the skin. After being embedded, slices are taken from the lesion, and are dyed to enhance intercellular elements of the cells. This is done, preferably, by haematoxylin and eosin.

One embodiment of the apparatus 14 for image acquisition is illustrated in FIG. 2. The slide 10, including a single dyed slice, is placed under a microscope 16, such as Olympus BX 40 system light microscope, using ×2, ×4, ×10, ×20, and ×40 lenses or compatible, where it is then photographed by a digital camera 18, such as Olympus Comedian C-2000 Zoom digital camera, or compatible. A plurality of images representing the slide at different magnifications are captured using various magnification lenses 20. The captured images are saved digitally and are then transferred to a computer. It will be appreciated that each photograph includes only a small portion of the slide at a particular magnification. In order to process the image of the entire slide, the photographs must be stitched together in the client and/or server computer. In a preferred embodiment of the present invention, after compression, preferably to a JPEG format, the compressed digitized data of the images is transferred by any communication means, such as Internet, to a remote server computer. This can be done by using e-mail or ftp.

In another embodiment of the invention, at least one image representing the slide is captured and then examined. It will be appreciated by a person skilled in the art that, in some cases, only one image representing the slide is sufficient for obtaining an analysis or/and diagnosis.

Figure 3:
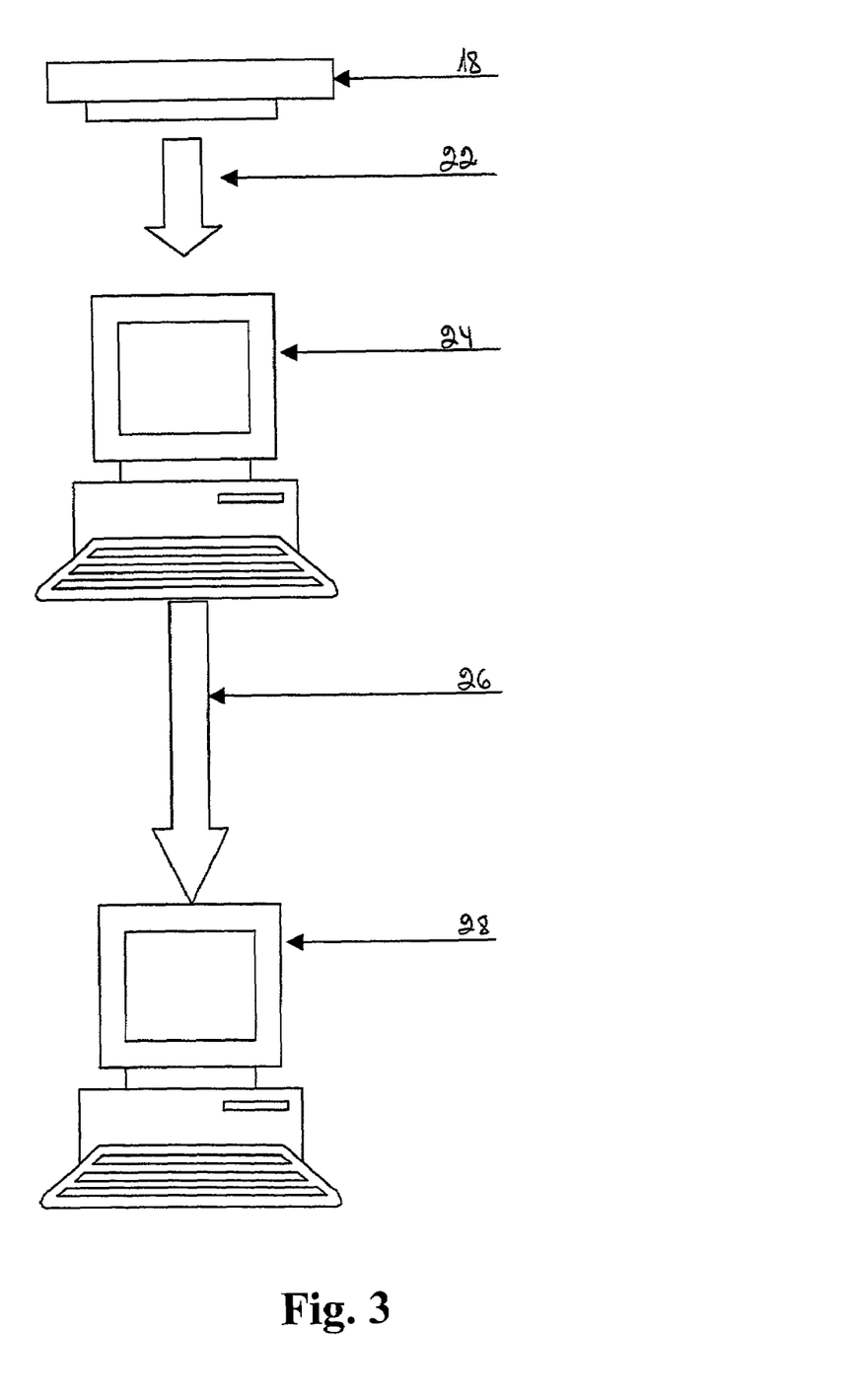
FIG. 3 is a flow chart illustrating the information flow from a digital camera to a server.

FIG. 3 illustrates the information flow from the digital camera to a server, according to one embodiment of the present invention, in which the Internet serves as a communication means. Alternatively, any other communication network which permits the transfer of digital images can be utilized. As can be seen, digital camera 18 generates digital images 22, which are stored in a client computer 24. From the client computer 24, the images are transferred via an Internet connection 26, or other communication network, to a remote server site computer 28, for diagnosis.

A novel technique of this patent is to simulate the pathologist's examination of the lesion and to point out how the diagnosis was reached. In order to achieve this, certain algorithms were developed. The purpose of the first two algorithms is to stitch together and overlap the pictures received from the camera, so as to form the complete slide, and then give the computer the ability of decreasing and increasing the magnification of the slide, as done when using a microscope. For the purpose of the present invention, the first algorithm is named Tesselation algorithm (1) (hereinafter: "TSA1"). The purpose of TSA1 is to combine together pictures taken at the same magnification.

Figure 4:
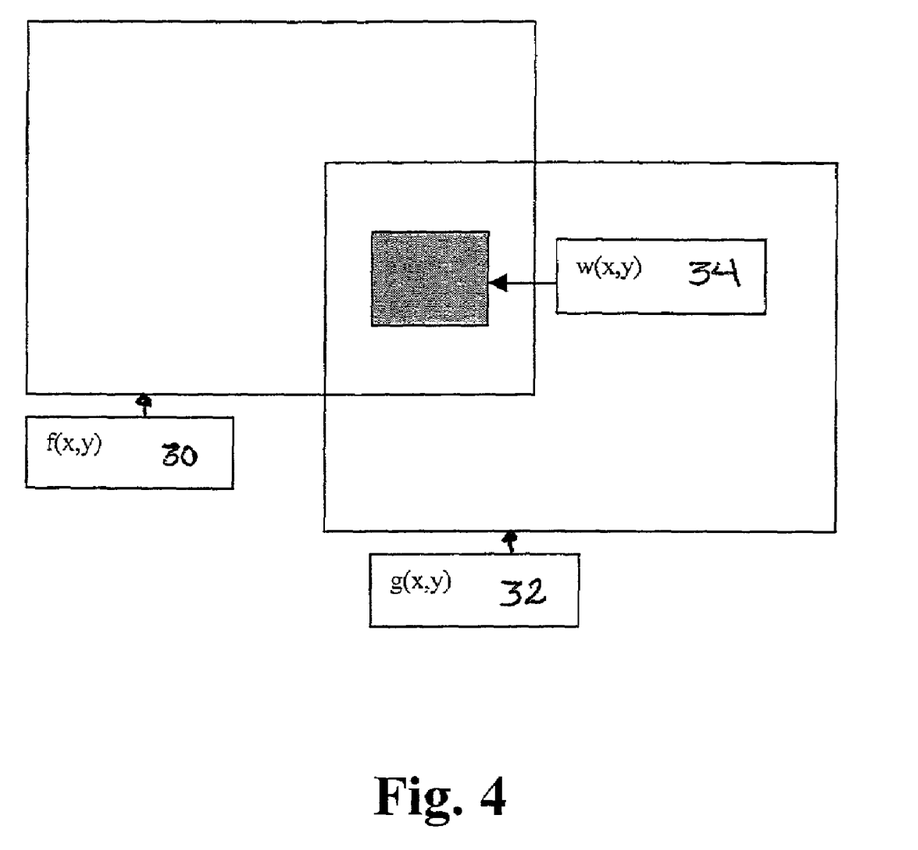
FIG. 4 is an illustration of two given images related to the step of stitching images.

Referring now to FIG. 4, there are shown two given images f(x,y) 30 of size M×N and g(x,y) 32 of size M×N. In order to stitch these images together, determination of the area w(x,y) 34 of size J×K where J<M and K<N such that w(x,y)⊂f(x,y) and w(x,y)⊂g(x,y) is required. Once this area is found, it is possible to join together the two images (where they overlap). Due to light differences, the overlapping area is generally similar but not exactly identical. When looking for one similar area in another, a common practice is to perform a correlation calculation between the two areas. The correlation coefficient (normalized due to sensitivity of amplitude or intensity variations) is defined as:

$$r(m,n) = \frac{\sum_{xy}\sum [f(x,y)-\overline{f}(x,y)][w(x-m,y-n)-\overline{w}]}{\sqrt{\sum_{xy}\sum [f(x,y)-\overline{f}(x,y)]^2 \sum_{xy}\sum [w(x-m,y-n)-\overline{w}^2]}}$$

Formula 1

We are looking for an area that appears in both images. It has been found that, taking a block in a size of 51×51 pixels from one image and moving it across the second image while calculating the correlation coefficient, it is possible to determine the exact location of the block. This is done for all the images of any specific magnification. The coordinates are then saved in a matrix at constant intervals.

The higher the correlation coefficient, the higher the probability that a match is found (−1<r<1). It was found that it is sufficient to take a 51×51 square of pixels from the two images (w). The position of w is taken by dividing the overlapping section of the two images at that iteration by two. This is done by using the correlation coefficient after reducing the images size and using the grayscale transform of the images.

Another mapping is generated after reducing each magnification to one below it and then pinpointing its position, so that a map recursively defining each image is obtained. For the purpose of the present invention the second algorithm which is responsible for this task is named Tesselation algorithm (2) (hereinafter: "TSA2").

The purpose of TSA2 algorithm is to establish a map enabling the computer to zoom in and out, by moving between images taken at different magnifications. Some features are detected best at different magnifications. Providing a map of the slide by learning the architectural layout of the lesion once, allows later reference back to the learnt architectural structure.

The TSA2 algorithm differs from the TSA1 in that we shrink the size of the smaller magnification so that the scales are equal. We then continue as in TSA1. Once this match has been found, its coordinates are stored in a matrix to be used later. These matrices are stored one above another. After termination of TSA2, the slide is mapped.

Another stage of preparation of the images is the detection of the background, performed by a third and a fourth algorithms. The purpose of the background algorithm is to detect the existence of a background and then remove it. In the context of the histopathological slides, background means anything that is not the lesion itself. For the purpose of the present invention, the term "background" includes also artifacts, such as dirt, dust etc. Two different algorithms for detecting the background were designed. One is suitable for smaller magnifications (×2–20), and the other is suitable for ×40 and higher magnifications.

The basis for both the algorithms is that, where the background exists, the standard deviation of the gray scale values is lowest. Both algorithms divide the slides into blocks, where a decision to continue to divide is based on the standard deviation. The holes are then closed and are merged together.

The following are functions performed by these algorithms on an image f(x,y) of size n×m pixels.
1. Divide f(x,y) into squares of size k×k where k<<n and k<<m and k/m=q and k/n=q where q is a whole number.
2. Calculate for all squares the standard deviation:

$$st=\Sigma(x_i-\overline{x})^2/(t-1)$$

where t=k*k and i=1..k*k.
3. For all squares lower than threshold, give value of background.
4. For all squares that do not belong to background, close areas that are surrounded by background.
5. Merge all areas of background together.

Another stage of the preparation of the images for processing is correction of the image intensity. Images acquired using a digital camera posses an effect of light spreading from the center of the image outwards, seen at lower magnifications. This is because the light is more powerful in the center covering that particular aperture. In order to get equal dispersion of the light, the images must be corrected. The procedure is as follows:
1. Each image f(x) from a low magnification is converted from RGB presentation to HSV (hue, saturation, value) presentation. What is important here is the Value. g(x)—Value
2. The center of gravity (sx,sy) is calculated:

sx=0;for i=1:n,for j=1:m sx=sx+g(i,j).*i;end;end;
   sx=sx/sum(sum(g));

sy=0;for i=1:n,for j=1:m sy=sy+g(i,j).*j;end;end;
   sy=sy/sum(sum(g));

3. The distance of each pixel from the center of gravity is calculated.
4. For each distance, the average is calculated. d—array of distances.
5. Let t=size(d), we are looking for g, such that, if linear regression on d(1:g) gives us error e1 and linear regression on d(g+1:t) gives us e2 then e1+e2 is minimum.
6. We now have an estimate of the dispersion of the light. We also know the breaking point of the light. We now fix the image, h(x)—the grayscale representation. If s=distance from center of gravity, for s<g h(x)=h(x)−d(s) and for s>g h(x)=h(x)+d(s).

After the processing module has prepared the images in order that an examination can be carried out, a list of pathological features is then examined and generated from the images. The feature list depends on the particular pathology being examined. See preferred embodiment for examples of features. This is done by using the image-processing engine.

When a pathologist manually looks at each slide, he looks for certain pathological criteria. Some of these features are only visible at higher magnifications. The process of examining the slide is very dynamic (and tedious)—magnifying only relevant areas that may be suspicious—containing information that maybe diagnostic, and then returning to the lower magnification.

There exists a list of known criteria for each pathological diagnosis. Some of these are clearly defined but are very difficult to quantify even for the expert, whereas some of these same features are relatively easily extracted by a computer with high accuracy. For example, the mean size of all pathological cells in a lesion can be very accurately measured by using digital imaging means, but almost impossible to measure manually. An expert's experience is judged by his ability to accurately score each feature in the list and to correctly weigh each feature according to its importance in overall assessment of the diagnosis. According to the present invention, the analysis module examines the features identified by the examining module, and gives them a score, at least partiallyu based on a comparison of images of prior cases stored in the database.

After scoring each feature in the feature list, all the scores are fed into an expert system decision maker. The expert system decision maker is a mixed expert system based on a number of techniques from the machine-learning field. The present invention's expert system has learnt the correct weights for each feature from a large set of cases of lesions diagnosed by a number of expert pathologists. This was done by using a principle component analysis by which features that were found to be correlating were first removed. The remaining features were then fed into a neural network using back propagation obtaining the weights for correct classification. The same process was repeated using basian networks, and a decision tree was built.

A novel technique of the present invention is the ability to conduct a "selected search" that a pathologist does automatically, and to switch between different magnifications when searching for the relevant information. To accomplish this, we have defined the process as thus.

1. Search for suspicious areas. A suspicious area is defined as an area that, when magnified, could show a pathological behavior. These areas are defined by heuristic rules developed by observation and instruction of an expert in the particular field of the examined pathology, such as known rules found in literature.
2. Let us say that n suspicious areas were observed. For each of the n suspicious areas found, magnify that area (using the map generated by TSA2) and then search the area for the relevant information (defined per pathology by expert in the field).

It will be appreciated that magnifying the area could mean not just by one magnification, but might even be up to the highest magnification.

For the analysis and diagnosis modules, a set of rules that can classify a case (rule-based system) was built. These rules were based on medical literature by the help of an expert. A classification of a specimen—in our case a slide, a decision is made based on a majority vote of the expert system mentioned, where more weight is given to the rules. This process is like a consultation of a number of experts, a common practice in medical diagnosis. An important note is that a result is not just a specific diagnosis, but also a measure of goodness of fit. In order to supply this measure, "fuzzy" variables are used giving us the ability to estimate the accuracy of the diagnosis and, in cases of unclear decisions, the possibility to advise what further tests must be done to confirm and increase the strength of the diagnosis.

Figure 5:
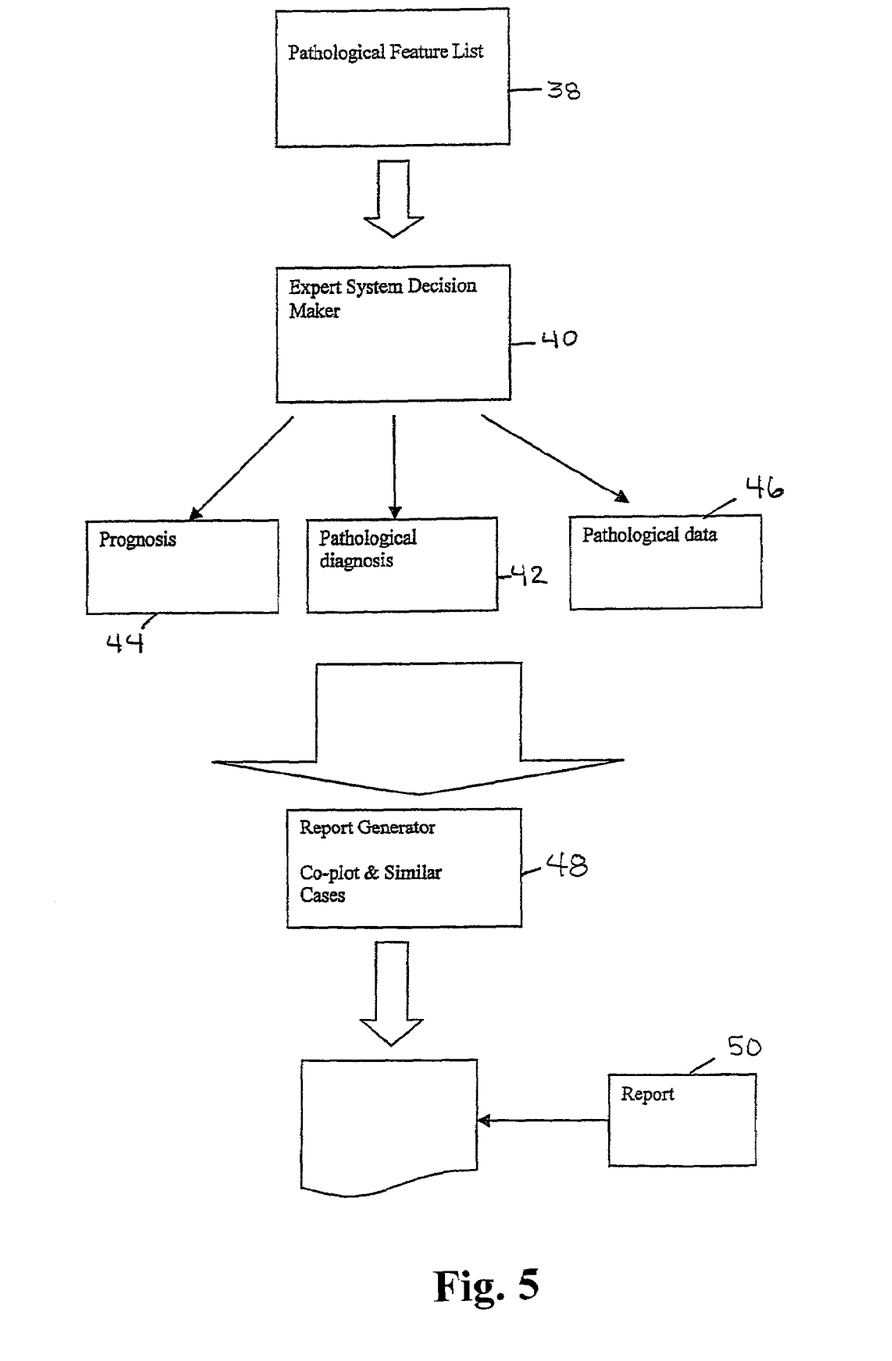
FIG. 5 is a flow chart showing the image processing of a slide.

A flow of information in the Expert System Decision Maker 40 is shown in FIG. 5. When the lesion is determined to be malignant, from the pathological feature list 38, a pathological diagnosis 42 is generated, and a prognosis 44 is estimated based on clinical and histopathological data 46. A report 50 is generated by report generator 48, depending on the particular report required.

The pathological features 38 are based on data from the images and from patient information such as age, sex, location. To extract the pathological features based on the images a number of operations have to be applied to the images. These operations are applied using the image processing engine.

Figure 6:
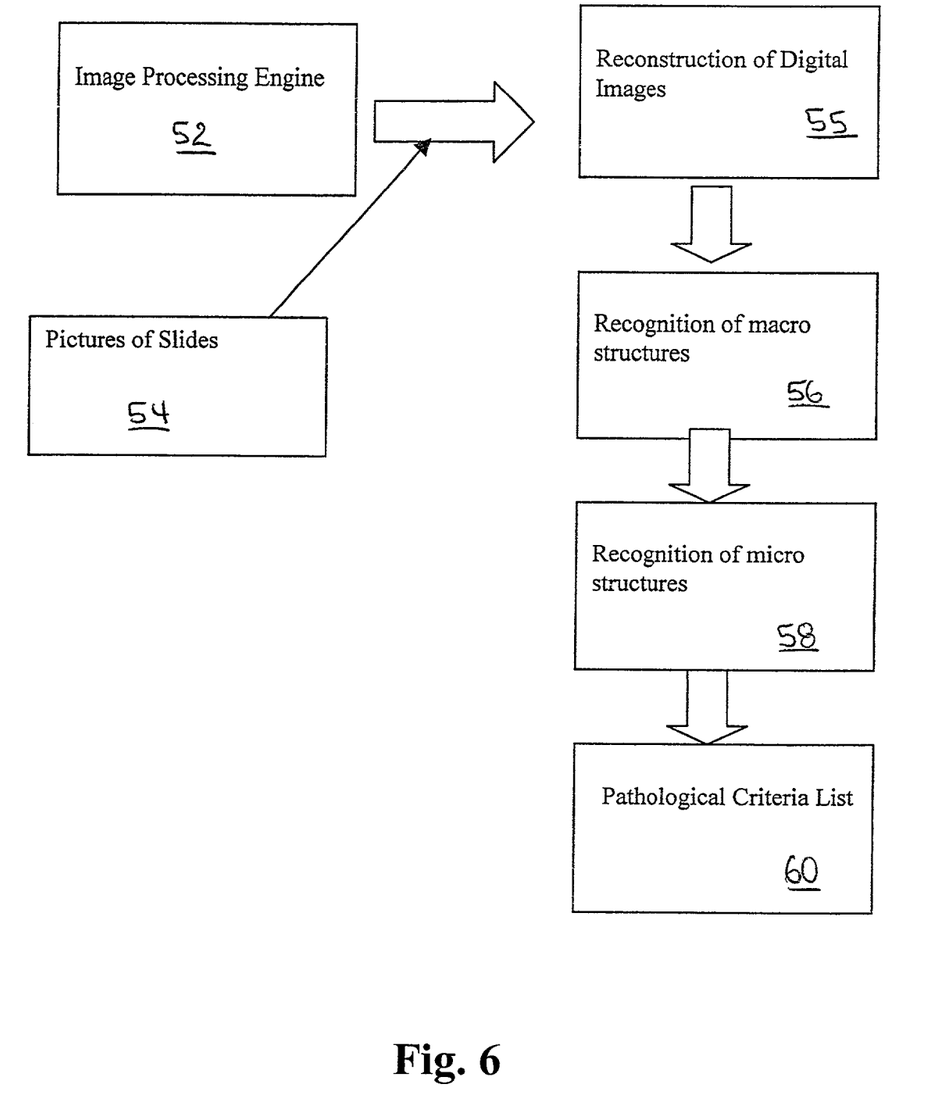
FIG. 6 is a block diagram showing the flow of information in the Expert System Decision Maker and the generation of a report.

FIG. 6 is an illustration of the operations of an image processing engine 52 for a slide. Pictures 54 of the slides to be examined are received by image processing engine 52, which reconstructs 55 the digital images, as described above. Two basic types of features are extracted from the images 55 received: those based on architectural changes 56 and those based on cellular changes 58 (in Melanoma mainly melanocyte cells). Architectural changes, or macro structures 56, can only be seen on a low magnification, where it is also important to detect what cells are making the architectural changes. A trained pathologist accomplishes this by his ability to recognize patterns based on prior experience and by occasionally zooming in (using higher magnification) to check what cells are making up that specific architecture. Thus, the system of the present invention segments the slide into the different layers using methods from the pattern recognition domain.

The following methods are used: First order statistics (mean, standard), Laws filters (energy calculated after filters are applied), moments, local binary pattern and contrast measure, DIFF4—Gray level difference histogram and Haralicks features: Energy, Homogeneity, Correlation, Correlation & Entropy (first calculated is the co-occurrency matrix normalized). These are trained using a perceptron network. This segmentation divides the slide into the various areas of the slide with a probability rate of its accuracy. In a preferred embodiment, among the areas and structures needing to be identified are the various layers of the skin and appendices. In the case of high uncertainty, individual cells maybe inspected at higher magnification at that particular location.

Cellular changes, or micro structures 58, can be seen mainly at higher magnifications. When looking for cell changes, first the cell information needs to be extracted. This means identifying cells at a higher magnification. A number of different cells and structures need to be recognized such as these in the exemplary embodiment: melanocyte (and nuclei), keratinocytes, erythrocytes cells, lymphocytes, melanin, collagen.

After the recognition of different structures and cells has been completed, the statistical information about particular cells is recorded and given a mark according to a previously learned scale. For example, the number of nuclei more than 10 microns in greatest diameter is recorded (after all nuclei of melanocytes are recorded) and according to our scale, the higher the number, the higher the mark (up to 10). This is done for each feature, and stored in a Pathological Criteria List 60, or a Pathological Feature List.

Figure 7:
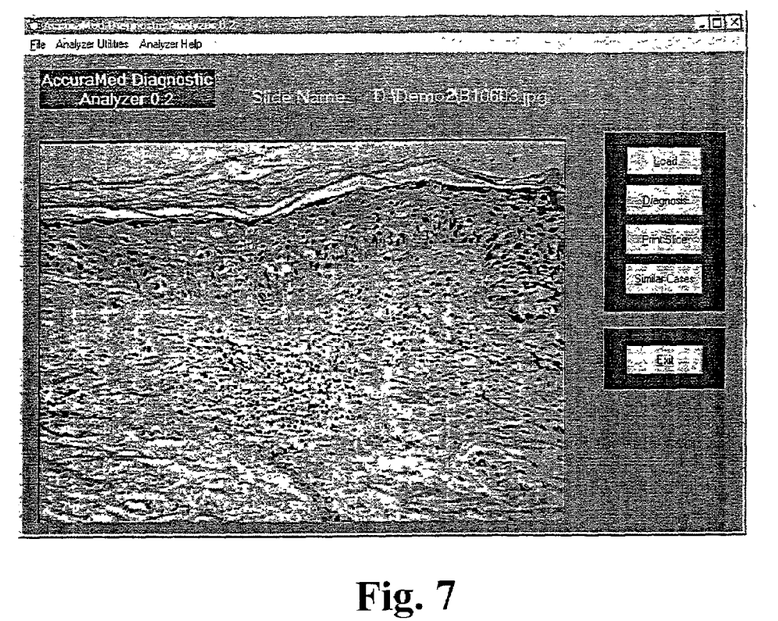
FIGS. 7–10 are illustrations of a report according to one embodiment of the invention.
Figure 8:
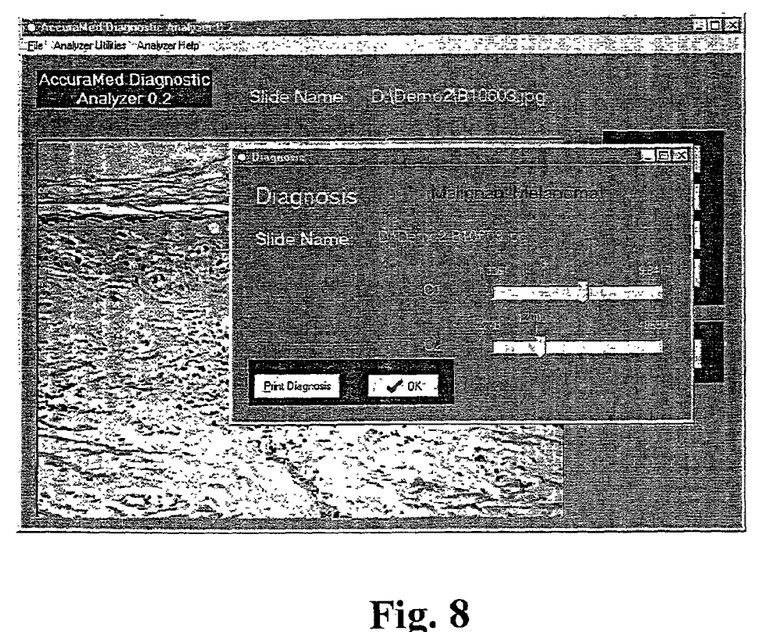

The next stage after these features have been fed into the expert system decision maker and diagnosis and prognosis have been made, a report 50 is generated. FIG. 5 further shows the generation of a report 50. The report (examples of whose contents shown in FIGS. 7–10) shows the patient information (name, sex, age, position of lesion), diagnosis, prognosis (if relevant) and relevant pathological data (a selection of the main features affecting the diagnosis). Main cell and architectural abnormalities (if existing) are shown visually on the images added to the report (see FIG. 7). Also generated is a Co-plot (shown in FIG. 10) showing where this case is in the feature space compared to other cases in our database. A comparison is made with the general norm in main feature categories. If requested, the images of similar cases are also added to the report (shown in FIG. 9). Another option, if requested, is a search for similar images, based on CBIR (Content Based Image Retrieval techniques). This is based on a database of statistical information of the slide, recording spatially localized color and texture features.

In an embodiment of the present invention, this report is then transferred back to the client via the Internet, or other communication network.

The co-plot method is a novel technique that the present invention uses in order to capture the configuration of the features at any given slide. It allows the system to elicit the similarity among pathological slides, both as a composite and as individual categories. Additionally, it allows the system to elicit the structure of the correlation among the various pathological features.

Classical multivariate analysis, such as principle component analysis or cluster analysis, usually analyzes either variables or observations (specimens) separately. The co-plot method of the present invention analyzes the two simultaneously. Using the present invention's novel graphic display technique, each specimen (observation) can be located within a two dimensional space. Furthermore, the location of each observation is determined by all variables (the quantitative mathematical representation of the pathological features), as will be described hereinafter. This space is named the "pathological features space".

Figure 10:
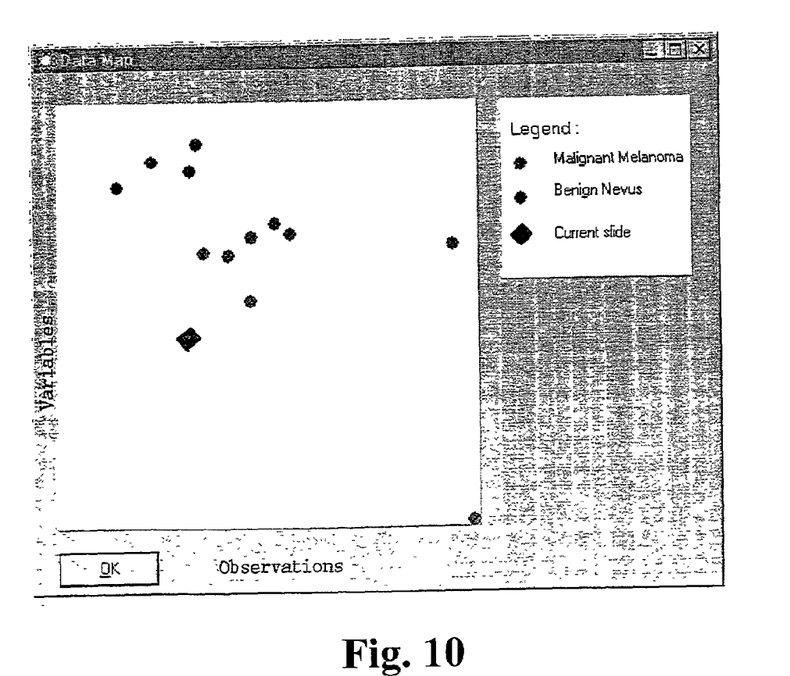

The Co-plot method of the invention is useful for the visual inspection of a large amount of data, represented in a n×m matrix (as shown in FIG. 10), where n is the number of observations (pathological slides) and m is the number of the variables per slide (pathological features). The co-plot method maps the observations (rows of the matrix) in such a way that similar observations are closely located to each other on the map, and represents each variable by an arrow. It thus enables a simultaneous study of observations and variables for a set of data. A measure of goodness of fit is computed and associated for each variable separately.

EXAMPLE

Figure 9:
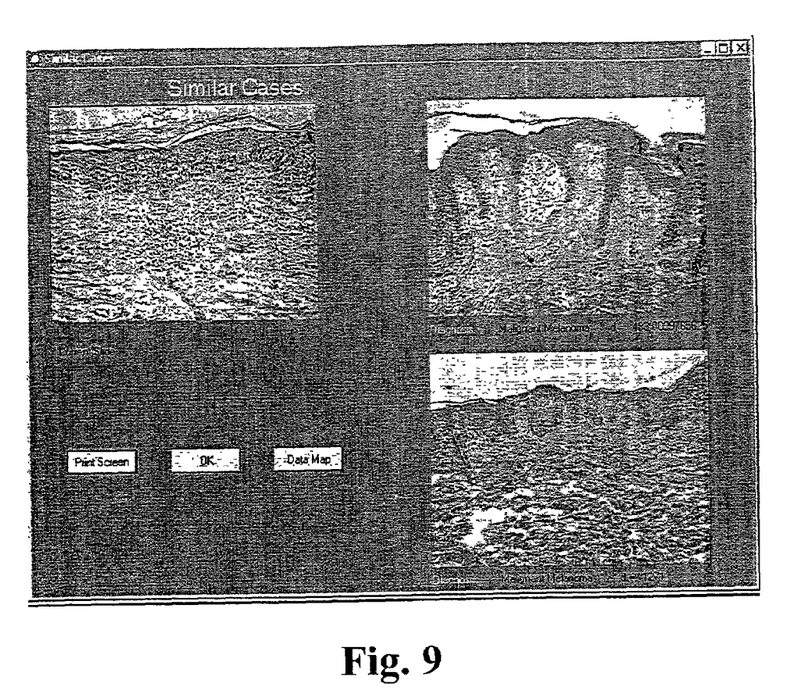

Sections of a tissue specimen to be examined were prepared. Their thickness was 3 μm. The slices were stained using the H&E (haematoxylin and eosin) method and embedded in paraffin. Approximately 10 images of each slice were acquired, using an Olympus BX 40 system light microscope, using ×2, ×4, ×10, ×20, and ×40 lenses. The microscope was connected to an Olympus Comedian C-2000 Zoom digital camera. The images were grabbed and stored in JPEG format. The file size was about 900 kb and the image dimension was 1600×1200 pixels. The file was transferred to a computer operating with the computer program product of the present invention. The program then stitched together and mapped the images using TSA1 and TSA2. Further, correction of background and image intensity algorithms were executed, resulting in images that are ready for computerized examination. The images were examined to score each feature in a list of predetermined criteria. After scoring each feature in the list, all the scores were fed into the expert system decision maker, which generated a report. FIGS. 7–10 are part of a report generated by the system. C1 and C2 are previously calculated attributes. FIG. 9 shows a search result for similar cases. FIG. 10 shows the co-plot result.

The following are descriptions of algorithms specifically developed for one of the preferred embodiments of the invention. This is basically an expansion of features generalized in the detailed description and given here in this particular preferred embodiment for detecting melanoma. As described, the slide goes through a number of stages when being processed. Some of these processes are general and some are specific.

Epidermis, Dermis and DEJ Detection

The Epidermis and Dermis are two layers of the skin that are very important for the detection of Melanoma. They give us the structural outlay of the skin that helps us detect certain cell elements whose appearance may differ or they might only appear in one and not the other. They themselves possess attributes that aid the diagnosis. The DEJ is the line that separates the Dermis from the Epidermis. In order to find the Dermis/Epidermis a number of features based on statistical pattern recognition were used. These include Haralicks features, first order statistics, Laws filters. For randomly drawn blocks, values were calculated and then were classified using the perceptron model (neural network), as known.

The detection of melanocytes is a process of a few stages.

Detecting Melanocytes in Epidermis

Melanocytes are very important cells in detecting Melanoma. Thus, melanocytes are sought in both the epidermis and in the dermis.

The algorithm for identifying melanocytes in epidermis is implemented using ×40 magnification. The basis for this algorithm is the observation that a melanocyte cell is made up of a nucleus and cell matter surrounding it. In the epidermis, because of fixation and shrinkage, the cell matter are white patches. To detect the cells, a search for possible nuclei is made, based on their color. By using morphological operations, a search is done to find where nuclei lie adjacent to cell matter (white spaces). After removing errors, the nuclei are paired with the patches and are recognized as one. At this stage, cell features are extracted (size of nuclei, size of cell . . . ).

Detecting Melanocytes in Dermis

The algorithm for identifying melanocytes in dermis is also implemented using ×40 magnification. The basis for this algorithm is that, in the Dermis, only the nucleus is clearly visible. What is also visible is the nuclei. The general shape of the nucleus of the Melanocyte is elliptic. Most Melanocytes appear together with the nuclei. Therefore, when searching for Melanocytes, we first search for nuclei, and then search for the nucleus in that neighborhood (60×60 pixels). The nuclei are found by taking a threshold of the image after a maximizing filter. The ellipse defining the nucleus is found on the threshold of the mean of the saturation. To find the ellipse, 2000 parameters that define an ellipse are randomly drawn, and the fittest are chosen for another round. Another population is generated from the best, leaving us finally with the best fitting parameters.

Melanin, Blood Detection

Melanin and blood are detected after filtering the image (smoothing), by using the certain color properties. Blood is bright red and melanin is brown. Because the color spaces are close, saturation is also used.

Nest Detection

Nests are groups of Melanocytes. When the Melanocytes are together, the cell matter (white patches) merge together, intertwined with nuclei. In order to detect nests, first Melanocytes are detected. Using cluster analysis (k-means) methods, the Melanocytes are clustered together forming a nest.

ASYMMETRY

This is done by finding the main layers, threshold them and then "flipping" them, obtaining their mirror and comparing the difference. Sometimes the image needs to be rotated according to the position of the lesion.

It will be appreciated by those skilled in the art that the invention is not limited to what has been shown and described hereinabove by way of example. Rather, the scope of the invention is defined solely by the claims which follow.

The invention claimed is:

1. A method for assisting in obtaining a pathological diagnosis from a plurality of pictures representing a specimen on a slide, the method comprising the following steps:
   obtaining digitized data corresponding to images of a specimen on a slide placed under a microscope;
   processing said images, wherein the step of processing comprises:
     combining pictures taken at a single magnification;
     enabling zooming in and out from each magnification to another; and
     detecting background and image intensity and correcting the images accordingly;
   examining the images in accordance with predetermined histopathological criteria; and
   providing an examination report based on said examination.

2. The method according to claim 1, further comprising: providing an analysis based on said examination.

3. The method according to claim 1, further comprising: providing a diagnosis based on said examination.

4. The method according to claim 1, wherein the step of obtaining digitized data includes obtaining digitized data corresponding to images of a specimen taken at at least one magnification.

5. The method according to claim 1, wherein the step of obtaining digitized data includes obtaining digitized data corresponding to images of a specimen taken at a plurality of different magnifications.

6. The method according to claim 5, further comprising mapping elements to permit zooming from images at one magnification to another at an analogous point in the images.

7. The method according to claim 1, wherein said specimen is taken from a tissue lesion.

8. The method according to claim 1, wherein said images are compressed in JPEG format.

9. The method according to claim 1, wherein the step of processing further comprises using TSA1.

10. The method according to claim 1, wherein the step of processing further comprises using TSA2.

11. The method according to claim 1, wherein said examination comprises determining the mean size of a pathological cell in said specimen.

12. The method according to claim 1, wherein said specimen comprises melanocytes, keratinocytes, erythrocytes, or lymphocytes.

13. The method according to claim 1, wherein said specimen comprises melanin or collagen.

14. The method according to claim 1, wherein said examination report comprises a co-plot.

15. The method according to claim 3, wherein said diagnosis is melanoma.

16. A medical decision support system for assisting in obtaining a pathological diagnosis from a plurality of pictures representing a specimen on a slide, according to the method of claim 1, said system comprising
   a computer; and
   a computer program product stored on a computer readable medium arranged to provide data derived from examination of digital images of a tissue specimen according to predetermined criteria for histopathological analysis.

17. A computerized medical decision support system as in claim 16 wherein said computer program product further includes an analysis module.

18. A computerized medical decision support system as in claim 17 wherein said computer program product further includes a diagnosis module.

19. A computerized medical decision support system as in claim 18 wherein said system further provides data concerning similar cases, including images and related information analysis.

20. A computerized medical decision support system as in claim 16, wherein said system further includes an image acquisition module for providing said digital images.

21. A computerized medical decision support system as in claim 20, wherein said image acquisition module includes:
   a microscope; and
   a digital camera coupled to said microscope for capturing, through said microscope, at least one picture representing a specimen on a slide and generating digitized images thereof.

22. The computerized medical decision support system as in claim 21, wherein said digital camera is arranged to capture, through said microscope, more than one picture representing a specimen on a slide and generating digitized images thereof.

23. A computerized medical decision support system as in claim 16, wherein said system further comprises
   a communication means for transferring data from a digital camera to a remote server for image processing, and from the server back to the computer.

* * * * *